US012027063B2

(12) United States Patent
Fey et al.

(10) Patent No.: US 12,027,063 B2
(45) Date of Patent: Jul. 2, 2024

(54) CONSTRAINT DEVICE AND METHOD OF TRAINING FOR USE OF LAPAROSCOPIC INSTRUMENTS

(71) Applicant: The Board of Regents of the University of Texas System, Austin, TX (US)

(72) Inventors: Ann Majewicz Fey, Dallas, TX (US); Diana Diesen, Dallas, TX (US); Husam Wadi, Richardson, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 419 days.

(21) Appl. No.: 16/932,547

(22) Filed: Jul. 17, 2020

(65) Prior Publication Data
US 2021/0020067 A1 Jan. 21, 2021

Related U.S. Application Data

(60) Provisional application No. 62/875,860, filed on Jul. 18, 2019.

(51) Int. Cl.
*G09B 23/28* (2006.01)
*A61B 1/313* (2006.01)
*A61B 90/57* (2016.01)

(52) U.S. Cl.
CPC .......... *G09B 23/285* (2013.01); *A61B 1/3132* (2013.01); *A61B 90/57* (2016.02)

(58) Field of Classification Search
CPC ........ G09B 11/02; G09B 23/28; G09B 23/30; B43L 15/00; A61B 90/57; A61B 90/60
See application file for complete search history.

(56) References Cited

U.S. PATENT DOCUMENTS 940,744 A * 11/1909 Smith .................... G09B 11/02
601/40
1,342,576 A * 6/1920 Wride ..................... B43L 15/00
401/6
(Continued)

FOREIGN PATENT DOCUMENTS

WO WO-2006097454 A1 * 9/2006 ............. A61B 90/60

OTHER PUBLICATIONS

R. Aggarwal, et al. "Laparoscopic skills training and assessment," British Journal of Surgery, vol. 91, No. 12, pp. 1549-1558, 2004.
(Continued)

*Primary Examiner* — Kurt Fernstrom
(74) *Attorney, Agent, or Firm* — POLSINELLI PC

(57) ABSTRACT

A passive constraint device is disclosed which attaches to a laparoscopic instrument to kinematically constrain the user from over-gripping the instrument and to train the user in proper handling of the instrument. Passive constraint devices include three degrees of freedom adjustment of a palm rest and clamps to the laparoscopic instrument. An active constraint device is disclosed which attaches to a laparoscopic instrument to dynamically constrain a user from over-gripping the instrument and provide resistive feedback to a user to train the user in proper handling of the instrument. Active constraint devices include a finger guard that, in one embodiment, is elastic and, in other embodiments, is solid but connects to finger loops of a laparoscopic instrument via elastic connectors. Methods of use include a method for training surgical residents in the proper handling of laparoscopic instruments using passive and active constraint devices during residency training.

20 Claims, 15 Drawing Sheets

(56) References Cited

U.S. PATENT DOCUMENTS

| | | | | |
|---|---|---|---|---|
| 1,783,657 | A * | 12/1930 | Kuntzleman | B43L 15/00 434/166 |
| 2,202,957 | A * | 6/1940 | Martin | B43L 15/00 401/8 |
| 4,163,536 | A * | 8/1979 | Heller | A61C 19/00 248/118 |
| 4,165,896 | A * | 8/1979 | Hunt | B43L 15/00 15/443 |
| 6,138,304 | A * | 10/2000 | Lipsky | A61B 90/60 5/643 |
| 6,704,959 | B2 * | 3/2004 | Schuerch | A61G 13/12 5/624 |
| 6,925,668 | B2 * | 8/2005 | Cuschieri | A61B 90/60 5/621 |
| 7,461,423 | B2 * | 12/2008 | Rutherford | F16M 11/2092 5/652 |
| 9,161,819 | B2 * | 10/2015 | Magelund | A61B 90/60 |
| 10,869,659 | B2 * | 12/2020 | Thommen | A61B 1/07 |
| 11,197,737 | B2 * | 12/2021 | Stefan | F16M 11/38 |
| 11,786,335 | B2 * | 10/2023 | Davies | B25J 1/02 606/1 |
| 2015/0064665 | A1 * | 3/2015 | Hunt | G09B 11/02 434/166 |
| 2021/0052260 | A1 * | 2/2021 | Estelle | A61B 17/00 |

OTHER PUBLICATIONS

D. Stefanidis, et al. "Psychomotor testing predicts rate of skill acquisition for proficiency-based laparoscopic skills training," Surgery, vol. 140, No. 2, pp. 252-262, 2006.
S. of American Gastrointestinal and E. Surgeons, "Fundamentals of laparoscopic surgery," www. flsprogram.org, Accessed Feb. 2018.
K. A. Zucker, et al., "Training for laparoscopic surgery," World journal of surgery, vol. 17, No. 1, pp. 3-7, 1993.
J. L. Emken, et al. "Training and assessment of laparoscopic skills," JSLS: Journal of the Society of Laparoendoscopic Surgeons, vol. 8, No. 2, p. 195, 2004.
T. P. Grantcharov, et al., "Randomized clinical trial of virtual reality simulation for laparoscopic skills training," British Journal of Surgery, vol. 91, No. 2, pp. 146-150, 2004.
K. E. Georgeson, et al. "Advances in minimally invasive surgery in children," The American journal of surgery, vol. 180, No. 5, pp. 362-364, 2000.
M. E. Linnaus, et al. "Complications in common general pediatric surgery procedures," in Seminars in pediatric surgery, vol. 25, No. 6. Elsevier, 2016, pp. 404-411.
D. El Azzouzi, et al. "Pediatric laparoscopic surgery," Journal of Medical and Surgical Research, vol. 1, No. 2, 2014.
C. A. Peters, "Complications in pediatric urological laparoscopy: results of a survey," The Journal of urology, vol. 155, No. 3, pp. 1070-1073, 1996.
E. Heijnsdijk, et al., "Slip and damage properties of jaws of laparoscopic graspers," Surgical endoscopy, vol. 18, No. 6, pp. 974-979, 2004.
E. P. Westebring-van der Putten, et al., "Force feedback requirements for efficient laparoscopic grasp control," Ergonomics, vol. 52, No. 9, pp. 1055-1066, 2009.
C. R. Wottawa, et al., "The role of tactile feedback in grip force during laparoscopic training tasks," Surgical endoscopy, vol. 27, No. 4, pp. 1111-1118, 2013.
T. Judkins, et al., "Effect of handle design and target location on wrist posture during aiming with a laparoscopic tool," in Proceedings of the Human Factors and Ergonomics Society Annual Meeting, vol. 48, No. 12. SAGE Publications Sage CA: Los Angeles, CA, 2004, pp. 1464-1468.
A. Trejo, et al., "Effect of handle design and target location on insertion and aim with a laparoscopic surgical tool," Applied Ergonomics, vol. 38, No. 6, pp. 745-753, 2007.
N. Ulhaq, et al. "Design and Evaluation of Haptic Constraints for Laparoscopic Instrument Handling," 2018 40th Annual International Conference of the IEEE Engineering in Medicine and Biology Society (EMBC), Honolulu, HI, USA, 2018, pp. 961-964, doi: 10.1109/EMBC.2018.8512421.
N. Wright, et al. "Evaluation of Surgical Performance after Extended Laparoscopic Training using Physical Haptic Constraints," 2022 9th IEEE RAS/EMBS International Conference for Biomedical Robotics and Biomechatronics (BioRob), Seoul, Korea, Republic of, 2022, pp. 01-07, doi: 10.1109/BioRob52689.2022.9925461.

* cited by examiner

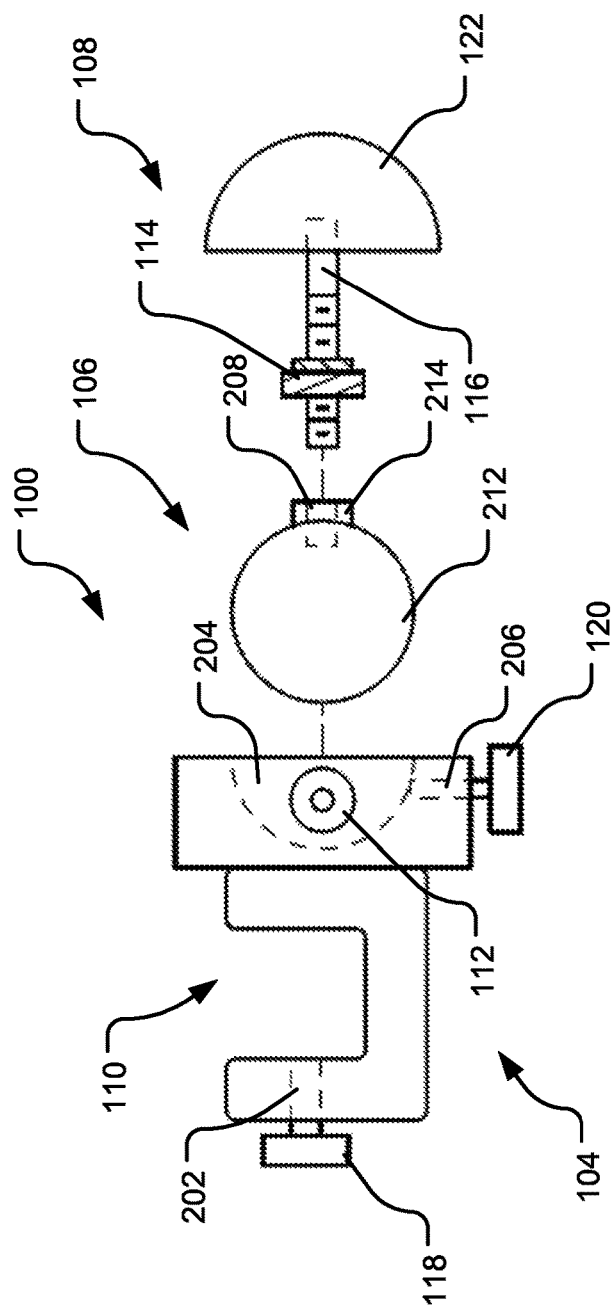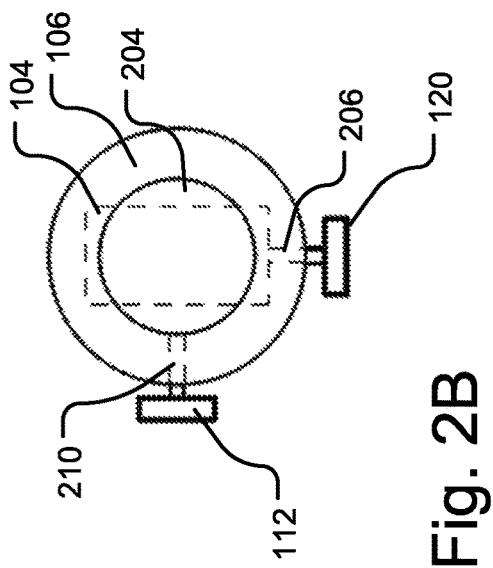

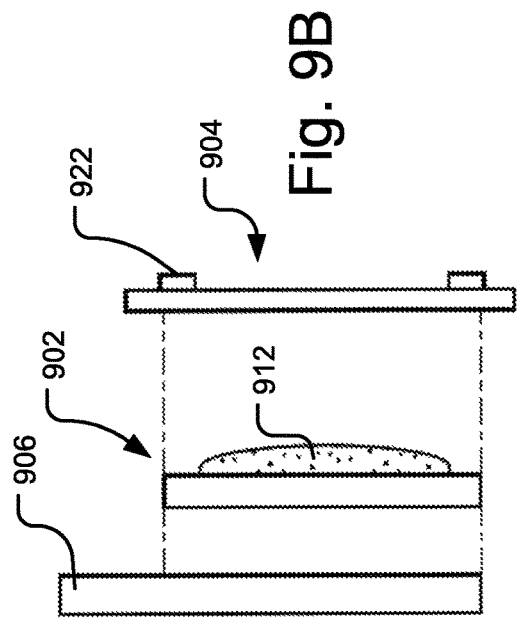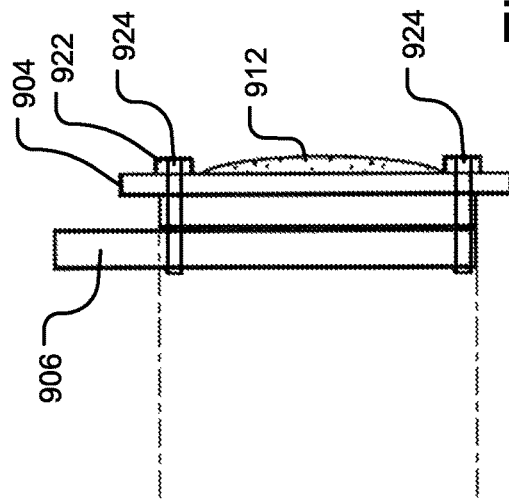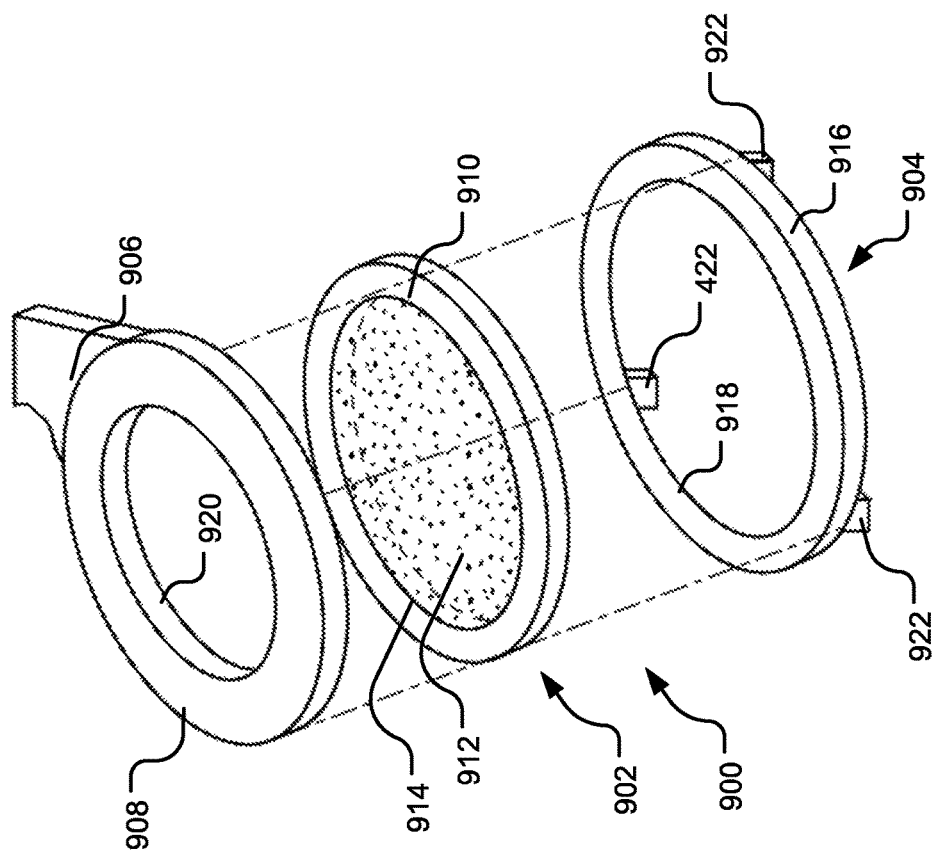

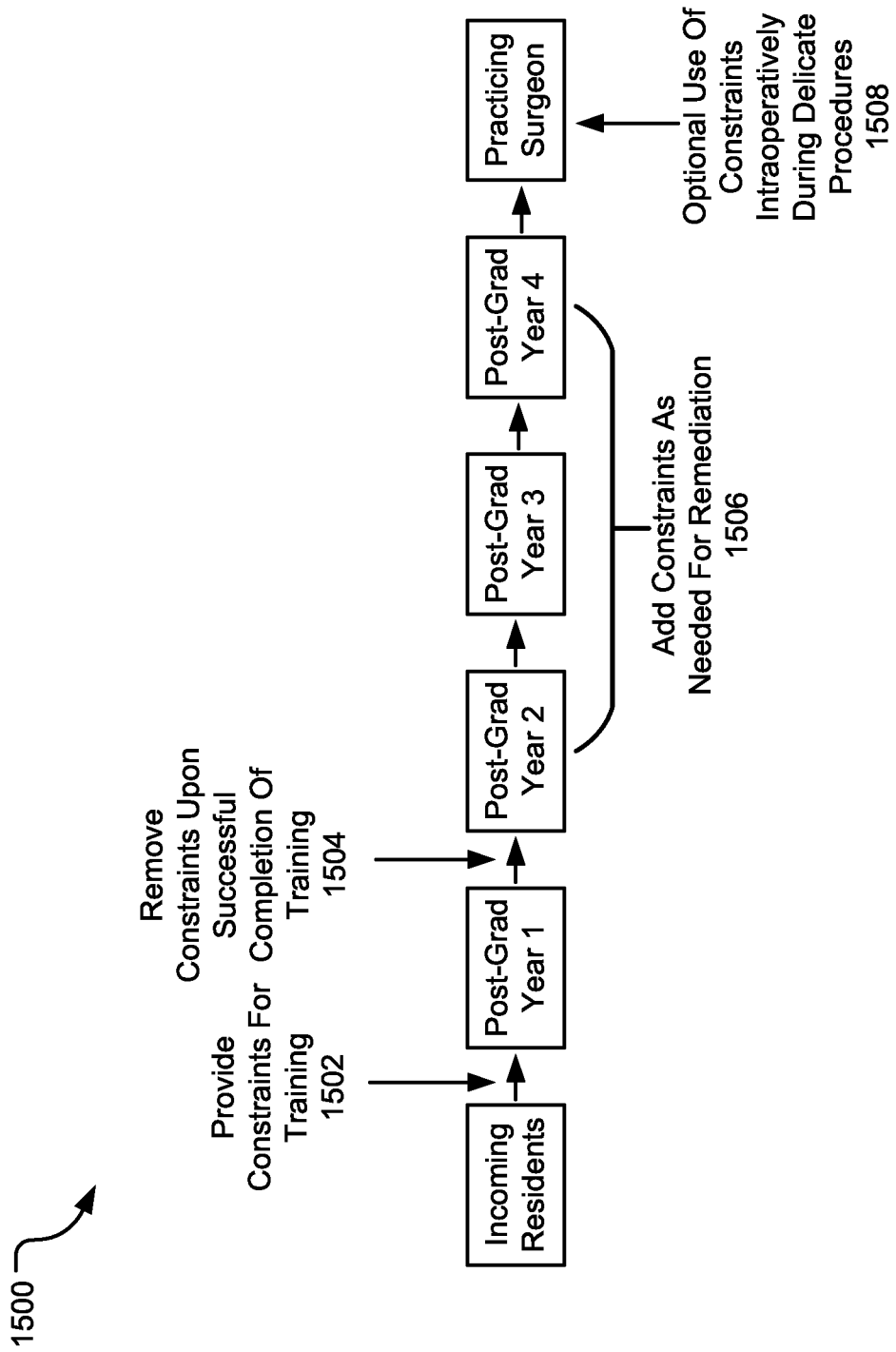

CONSTRAINT DEVICE AND METHOD OF TRAINING FOR USE OF LAPAROSCOPIC INSTRUMENTS

PRIORITY

The present application claims the benefit of U.S. Provisional Patent Application No. 62/875,860, filed Jul. 18, 2019 and entitled "CONSTRAINT DEVICE AND METHOD OF TRAINING FOR PROPER HANDLING OF LAPAROSCOPIC INSTRUMENTS," the content of which is expressly incorporated herein by reference in its entirety.

BACKGROUND

1. Field

Embodiments of the present invention generally relate to medical devices, and more specifically to devices and methods for training surgeons to use laparoscopic tools during a medical procedure.

2. Discussion of Related Art

The use of laparoscopic instruments requires excellent hand-eye coordination, precise spatial reasoning skills, and the automation of non-intuitive arm movements. As a result, extensive training of prospective surgeons has been developed to assist in learning and practicing these skills in non-patient settings, including training programs, bench-top models, and even virtual reality simulators. Learning and mastering of laparoscopic skills may be an involved and complicated process, especially for pediatric residents who must additionally learn how to operate on fragile tissues and within extremely small spaces. Given these operative conditions, precise, controlled, and gentle laparoscopic tool motions is critical.

Despite the training necessary, proper handling and ergonomics of laparoscopic tools is often overlooked when training novice surgeons. As a result, laparoscopic tools are often over-gripped, which may result in excessive application of force and potential surgical complications through decreased tool stability. Further, over-gripping during a laparoscopic surgery may result in tissue damage or other surgical damage, often due to lack of haptic feedback when compared to open surgery.

To address this issues, techniques and devices have been developed to provide tactile feedback from a laparoscopic tool to provide better information to a surgeon about gripping forces. However, such techniques and devices often require the use of an external sensor on the tip of the tool and do not address issues related to tool stability and control. Redesigns of laparoscopic instruments have also been proposed. However, such redesigned tools provide drawbacks in effectiveness to accomplish the surgical task for which the tool is used.

BRIEF SUMMARY

One aspect of the present disclosure relates to a mechanical device that enables proper laparoscopic instrument handling and method of use during training. In some implementations, correction of over-grip of existing laparoscopic instruments is addressed. In one embodiment, a constraint mechanism may be a passive constraint kinematically preventing the user of a laparoscopic tool from over-gripping the tool. The passive constraint may include a clamp for attachment to the laparoscopic instrument and a three degree-of-freedom adjustable palm rest for positioning the laparoscopic instrument to effect kinematic control of finger position and proper grip of the instrument. Another embodiment may include an active constraint mechanism that provides dynamic resistive control actively providing resistive force feedback to the user if over-grip occurs. The active constraint mechanism may include an elastic or other flexible membrane to resist the user' grip and may be secured to a finger loop of the laparoscopic tool via a solid clip or other attachment device. Another example of the active constraint mechanism may be secured to the finger loop of the laparoscopic tool via a set of elastic connectors.

In another aspect of the present disclosure, a general method for using the passive and/or active constraints of the laparoscopy tools in a training program for proper handling of the laparoscopy tools in surgery is provided. The method may include the operation of controlling a laparoscopic instrument during a procedure with a constraint device attached to the laparoscopic instrument, the constraint device restricting extension of an instrument operator's fingers through a finger hole of the laparoscopic instrument to for proper grip of the laparoscopic instrument during operation.

The aforementioned may also be achieved in an aspect of the present inventive concept by providing a finger guard and an attachment clip, the attachment clip orienting the finger guard over the finger hole when attached to the laparoscopic instrument. The finger guard may be composed of a flexible material and provides a resistive force against the instrument operator's fingers during control of the laparoscopic instrument. The attachment clip may include a circular frame and an attachment prong extending from the circular frame and the attachment prong may include a flared end opposite the circular frame to hold the attachment clip and the finger guard to the finger hole of the laparoscopic instrument.

The finger guard may, in another embodiment, be composed of an inflexible material and the attachment clip includes a circular frame and a plurality of attachment protrusions extending from the circular frame. The constraint device may further include an elastic connection band extending between the plurality of attachment protrusions and over the finger hole to hold the attachment clip and the finger guard to the finger hole of the laparoscopic instrument.

The aforementioned may also be achieved in an aspect of the present inventive concept by providing the constraint device with a clamp portion attaching the constraint device to the laparoscopic instrument, a joint attached to the clamp portion, and a palm contact attached to joint. The joint may include a ball and a socket joint with three degrees of freedom of movement. The palm contact may include a palm rest and a palm rest stem extending from the palm rest and attaching to the joint and a palm rest stem has an adjustable length. The joint may also include an adjustment screw and locking of the ball of the joint in the orientation within the socket joint includes rotating the adjustment screw.

The aforementioned may also be achieved in an aspect of the present inventive concept by providing orienting the ball of the joint to locate the palm rest in a center of an operator's palm and locking the ball of the joint within the socket joint in an orientation obtained from the orienting of the ball of the joint. The aforementioned may also be achieved in an aspect of the present inventive concept by providing adjusting a length of the palm rest stem to contact an operator's palm and setting, via a locking nut disposed on the palm rest stem, the length of the palm rest stem.

The foregoing is intended to be illustrative and is not meant in a limiting sense. Many features of the embodiments may be employed with or without reference to other features of any of the embodiments. Additional aspects, advantages, and/or utilities of the present inventive concept will be set forth in part in the description that follows and, in part, will be apparent from the description, or may be learned by practice of the present inventive concept.

BRIEF DESCRIPTION OF THE DRAWINGS

The description will be more fully understood with reference to the following figures and data graphs, which are presented as various embodiments of the present inventive concept and should not be construed as a complete recitation of the scope of the present inventive concept, wherein:

FIG. 2A illustrates an exploded side view of a passive constraint device for a laparoscopic instrument according to one or more aspects of the present disclosure;

FIG. 2B illustrates an end view of a mounting portion and a spherical joint portion of a passive constraint device for a laparoscopic instrument according to one or more aspects of the present disclosure;

FIG. 9A illustrates an exploded isometric view of a second active constraint device for a laparoscopic instrument according to one or more aspects of the present disclosure;

FIG. 9B illustrates an exploded side view of a second active constraint device for a laparoscopic instrument according to one or more aspects of the present disclosure;

FIG. 9C illustrates an assembled side view of a second active constraint device for a laparoscopic instrument according to one or more aspects of the present disclosure;

FIG. 15 is diagram showing a method of training surgical residents in the use of laparoscopic instrument handling during residency, and interoperatively, incorporating passive and active constraint devices in accordance with embodiments of the present disclosure.

DETAILED DESCRIPTION

Figure 1:
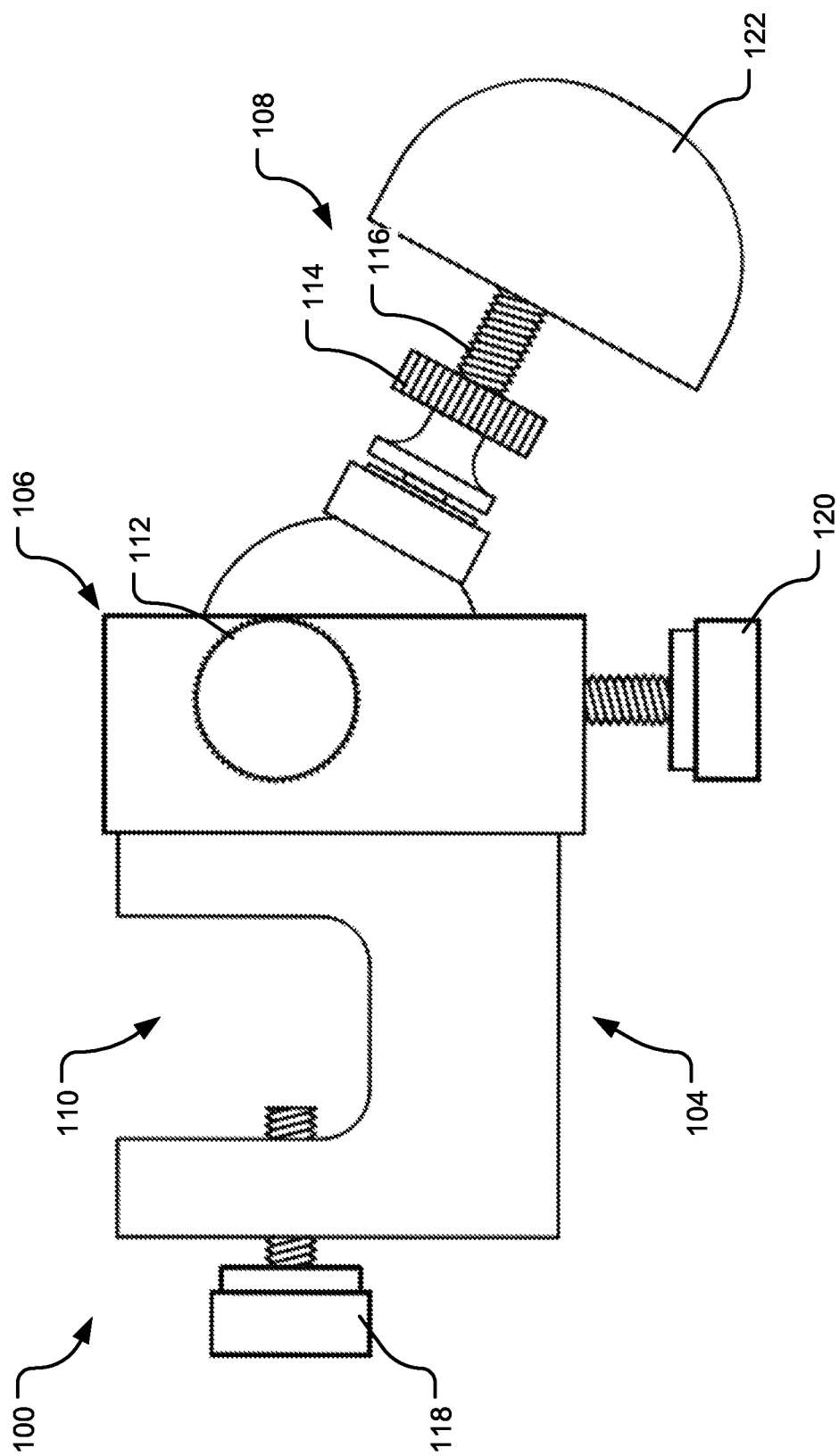
FIG. 1 illustrates a side view of a passive constraint device for a laparoscopic instrument in accordance with an embodiment of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims. Further, it should be understood that any one of the features of the present inventive concept may be used separately or in combination with other features. Other systems, methods, features, and advantages of the present inventive concept will be, or become, apparent to one with skill in the art upon examination of the figures and the detailed description. It is intended that all such additional systems, methods, features, and advantages be included within this description, be within the scope of the present inventive concept, and be protected by the accompanying claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

Any term of degree such as, but not limited to, "substantially," as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees.

The term "coupled" is defined as connected, whether directly or indirectly through intervening components, and is not necessarily limited to physical connections. The connection can be such that the objects are permanently connected or releasably connected. The terms "comprising," "including" and "having" are used interchangeably in this disclosure. The terms "comprising," "including" and "having" mean to include, but not necessarily be limited to the things so described. The term "real-time" or "real time" means substantially instantaneously.

Lastly, the terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps or acts are in some way inherently mutually exclusive.

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

In the description of the embodiments and experimental details that follows, the terms "laparoscopic tool" and "laparoscopic instrument" are synonymous and incorporate laparoscopic instruments that are either in-line, angled or have a pistol grip and have at least one of a finger loop (or ring) or a thumb loop (or ring). Laparoscopic tools also include but are not limited to Cannulas and Trocars, Trocar Incision Closure Devices, Electrodes and Electrosurgical Cables, Laparoscopic Bipolar Scissors and Graspers, Forceps and Graspers, Hooks and Probes, Knot Pushers, Needles and Needle Holders, Rigid Scopes, Retractors, and Scissors. The term active constraint means that the constraint embodiment provides active force feedback to the user, in relation to the amount of over-grip on the tool. The term passive constraint means that the constraint embodiment physically prevents the user from over-gripping the instrument. The term over-grip (or over-gripping) means that the user grasps the finger loops of the instrument with more than just the tips of their fingers. A resistive control or a resistive constraint means that the constraint in some way provides resistive feedback to the user based on tool over grip.

II. General Architecture

Figure 3A:
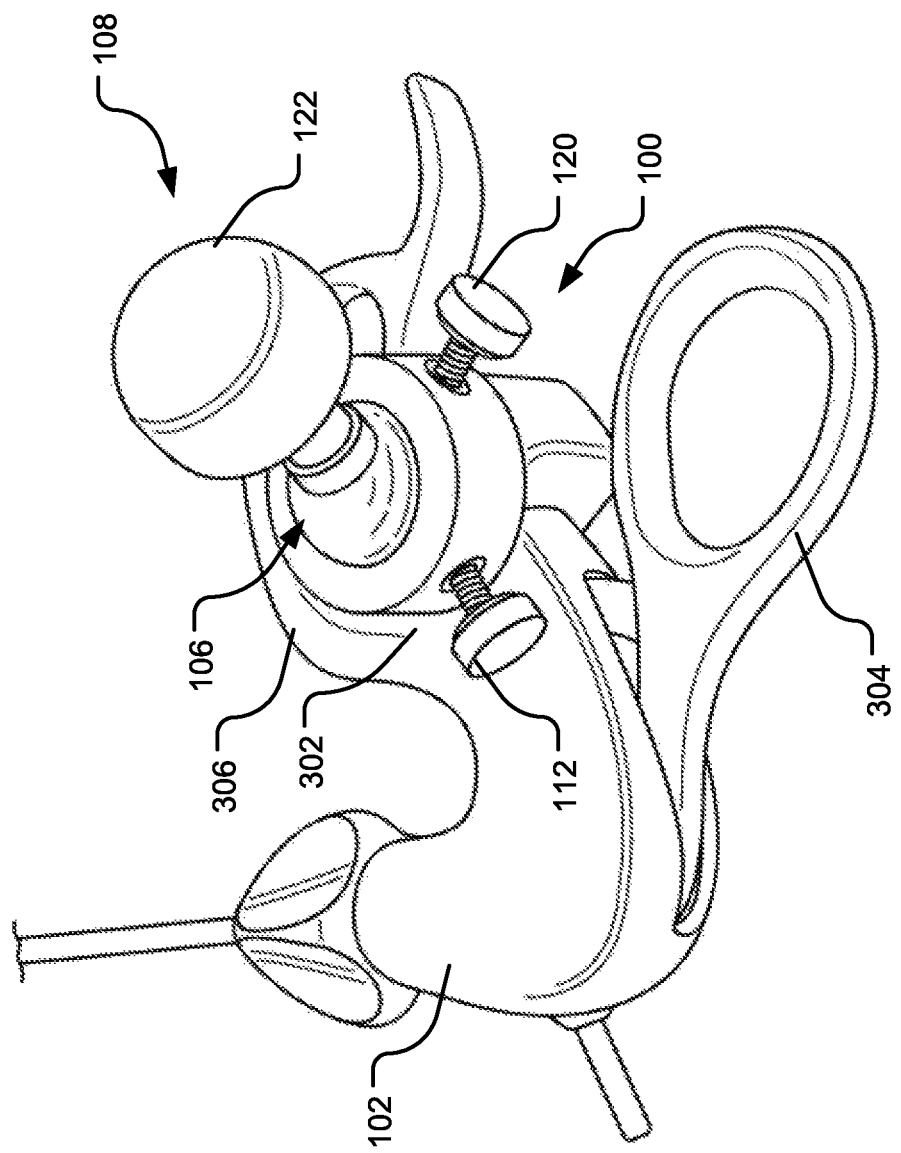
FIG. 3A illustrates a passive constraint device attached to the laparoscopic instrument according to one or more aspects of the present disclosure.
Figure 3B:
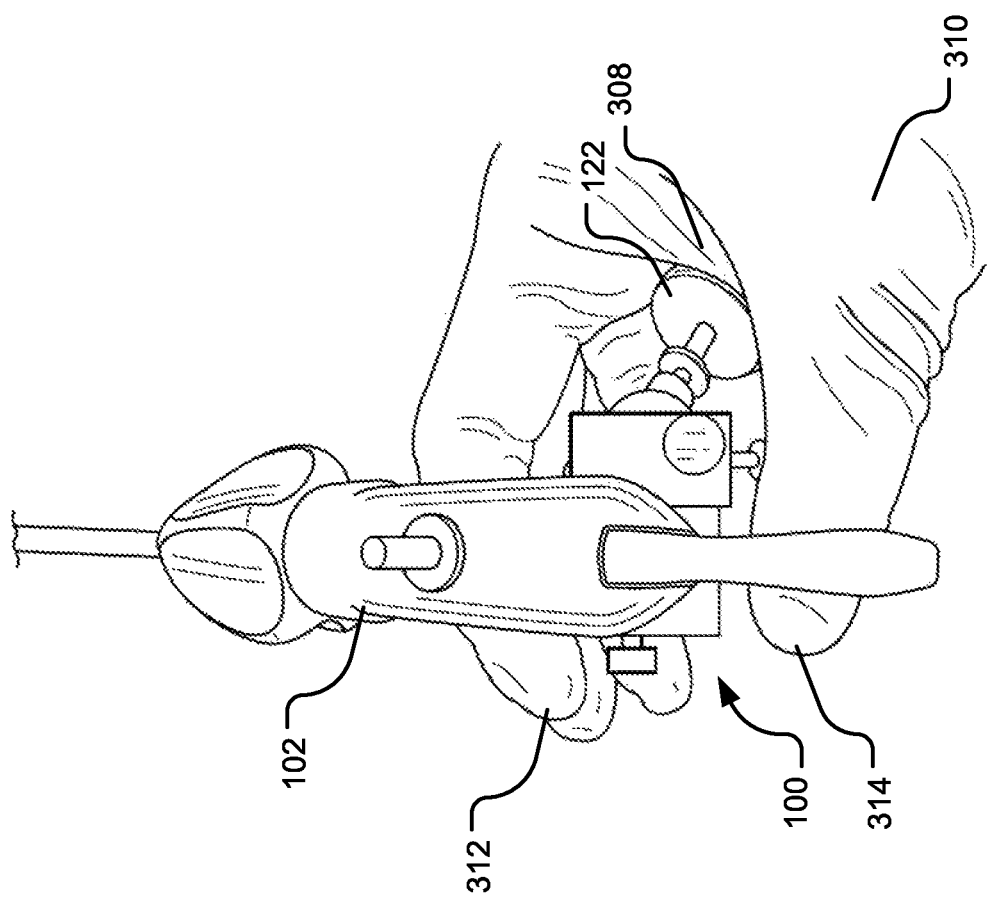
FIG. 3B illustrates a passive constraint device attached to the laparoscopic instrument and in use according to one or more aspects of the present disclosure.

The disclosure now turns to FIGS. 1-3B to illustrate one embodiment of a passive constraint device 100 for a laparoscopic instrument 102 in accordance with aspects of the present disclosure. In particular, FIG. 1 illustrates a side view of a passive constraint device 100, FIG. 2A illustrates an exploded side view of the passive constraint device 100, FIG. 2B illustrates an end view of the passive constraint device 100, FIG. 3A illustrates the passive constraint device 100 attached to the laparoscopic instrument 102, and FIG. 3B illustrates the passive constraint device 100 attached to the laparoscopic instrument 102 and in use. In general, the passive constraint device 100 may attach to a laparoscopic instrument 102 to kinematically prevent the user of the laparoscopic tool from over-gripping the tool when being held. In particular, the passive constraint device 100 may contact the palm or other part of the user's hand to prevent the user from locating the tool 102 near the palm of the user. When attached to the laparoscopic instrument 102, the passive constraint device 100 causes the user of the tool to properly grip the tool for efficient and effective use during a surgical procedure.

In general and as illustrated best in FIGS. 1-2B, the passive constraint device 100 may include mounting portion 104, a spherical joint portion 106, and a palm contact portion 108. The mounting portion 104 may include an attachment mechanism for attaching the passive constraint to a laparoscopic instrument 102 or other surgical tool. In one particular implementation, the mounting portion 104 includes a C-shaped receiver 110 and an adjustable clamp screw 118 passing through C-shaped receiver 110 via a threaded clamp screw hole 202 passing through an arm of the receiver at the rear of the passive constraint device 100. Rotation of the clamp screw 118 in a first direction may extend the screw through the hole and into an interior area of the C-shaped receiver 110. Rotation of the clamp screw 118 in an opposite direction may retract the clamp screw from the interior area. To attach the passive constraint device 100 to the laparoscopic instrument 102 and as shown in FIGS. 3A and 3B, a portion of the tool may be located within the C-shaped receiver 110 and the clamp screw 118 may be tightened to apply a locking force onto the tool portion to hold the passive constraint device 100 onto the laparoscopic instrument 102. It should be appreciated that other attaching mechanisms may be integrated with the passive constraint device 100 to attach the constraint to the laparoscopic instrument 102 or other type of surgical or medical tool. In some instances, the C-shaped receiver 110 may be configured or molded to fit different types of medical tools or customized to receive a particular type and style of medical tool.

The passive constraint device 100 may also include a spherical joint portion 106 attached to the mounting portion 104 on an end distal of the clamp screw 118. In one implementation, the spherical joint portion 106 may include a ball-and-socket joint, allowing for three degrees of freedom adjustability. As shown in FIGS. 2A and 2B, the spherical joint portion 106 may thus include a ball 212 located within a socket 204 of the passive constraint device 100. The ball 212 may be locked or otherwise held in a particular orientation within the socket 204 by one or more adjustment screws extending through an outer wall of the passive constraint device 100 and into the socket 204. In one particular implementation illustrated in FIGS. 1-2B, a lower adjustment screw 120 may extend vertically, via vertical threaded hole 206, into the socket 204 and a side adjustment screw 112 may extend, via horizontal threaded hole 210, horizontally into the socket 204. Similar to the clamp screw 118 above, rotation of the adjustment screws 112, 120 in a first direction may extend the screw through the corresponding hole 206, 210 and into the socket 204 and rotation in an opposite direction may retract the adjustment screw from the socket. When extending into the socket 204, the adjustment screws 112, 120 may apply a clamping force onto the ball 212 to hold the ball in position. In this manner, the ball 212 may be rotated through the three degrees of freedom and locked into place by one or more of the adjustment screws 112, 120.

The palm contact portion 108 of the passive constraint device 100 may attach to and extend from the ball 212 of the spherical joint portion 106. In one implementation, the palm contact portion 108 may include a half-sphere shaped palm rest 122, a threaded palm rest post 116, and a locking nut 114 rotatable around the palm rest post 116. The ball 212 may include a threaded mounting hole 208 configured to receive the corresponding threaded palm rest post 116 so that the palm contact portion 108 may mount to and extend from the ball 212. In addition, the ball 212 may include a threaded ring 214 disposed around the edge of the threaded mounting hole 208 for threadably receiving the locking nut 114 on the palm rest post 116. The locking nut 114 may freely rotate around the palm rest post 116 to engage with the threaded ring and further lock the palm contact portion 108 to the ball 212 through rotation of the locking nut 114 in a first direction. Disengaging the palm contact portion 108 from the ball 212 may include rotating the locking nut 114 in the opposite direction to disengage the locking nut from the threaded ring 218 and rotating the whole of the palm contact portion 108 to disengage the threaded palm rest post 116 from the threaded mounting hole 208.

FIG. 3A illustrates the passive constraint device 100 discussed above attached to laparoscopic instrument 102 at a body portion 302 in between the thumb loop 304 and the finger loop 306. More particularly, the passive constraint device 100 clamps to the body portion 302 of the laparoscopic instrument 102 through the mounting portion 104 of the passive constraint. To attach the passive constraint device 100, an operator may locate the body portion 302 of the laparoscopic instrument 102 in the C-shaped receiver 110 and adjust the clamp screw 118 to engage the body portion 302 and clamp the passive constraint device 100 against the laparoscopic instrument 102. The passive constraint device 100 may be mounted such that the palm contact portion 108 extends to the right of the laparoscopic instrument 102 (for right-handed operators of the tool) or such that palm contact portion 108 extends to the left of the laparoscopic instrument 102 (for left-handed operators of the tool). FIG. 3B illustrates the passive constraint device 100 attached to the laparoscopic instrument 102 and in use. In particular, FIG. 3B illustrates a right-handed operator of the laparoscopic instrument 102 such that the passive constraint device 100 is clamped to the tool with the palm contact portion 108 extending to the right of the tool. In use, the palm rest 122 contacts a palm area 308 of a right hand 310 of the operator, with one or more fingers 312 protruding through finger loop 306. As shown, the passive constraint device 100 may prevent the user's fingers 312 and/or thumb 314 from extending fully through the respective finger holes of the laparoscopic instrument 102, demonstrating the proper grip to be used with the laparoscopic instrument 102.

Further, one or more aspects of the passive constraint device 100 may be adjusted for proper and comfortable placement of the palm rest 122 into the palm 308 of the user's hand 310. For example, adjustment screws 112, 120 may be loosened and the ball 212 may be adjusted within the three degrees of freedom to locate the palm contact portion 108 into the user palm 308. Tightening of the adjustment screws 112, 120 may lock the position of the ball 212 in the selected orientation. The length of the palm rest post 116 may also be adjusted through the engagement of the locking nut 114 with the threaded ring 214. These adjustment mechanisms may orient the palm rest 122 into the user's palm 308 to demonstrate the proper grip for using the laparoscopic instrument 102.

In one particular implementation, the passive constraint device 100 may be constructed of three-dimensional printed plastic. The palm rest 122 may be a combination of a hard plastic (to allow for a solid assembly) and a soft rubber-like material on the outer surface of the palm rest for comfort to the user. The length of the palm rest post 116 may be adjustable from about 1.632 inches to 2.295 inches and may also be rotated to fit securely with the user's hand 310. In some implementations, the diameter of the palm rest 122 may be 0.875 inches and the diameter of the ball 212 may be 0.7 inches. The clamp screw 118 and/or the adjustment screws 112, 120 may be #6-32 screws of varying lengths. While the embodiment of the passive constraint device 100 illustrated has been constructed with the particular dimensions and shapes, the passive constraint device 100 of the present disclosure should not be limited to such sizes, or even scaled in a precise manner. In the spirit of the present disclosure, there are many different types of laparoscopic instruments 102 for which the clamp width may vary and many different users for which the shape, height and size of the palm rest 122 may vary.

Figure 4:
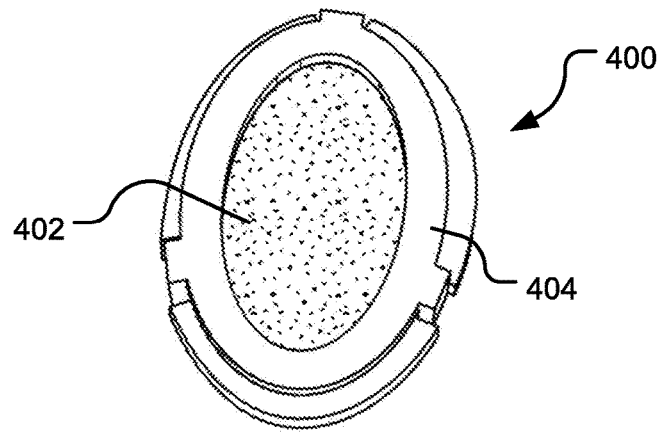
FIG. 4 illustrates a front view of an active constraint device for a laparoscopic instrument in accordance with an embodiment of the present disclosure.
Figure 5:
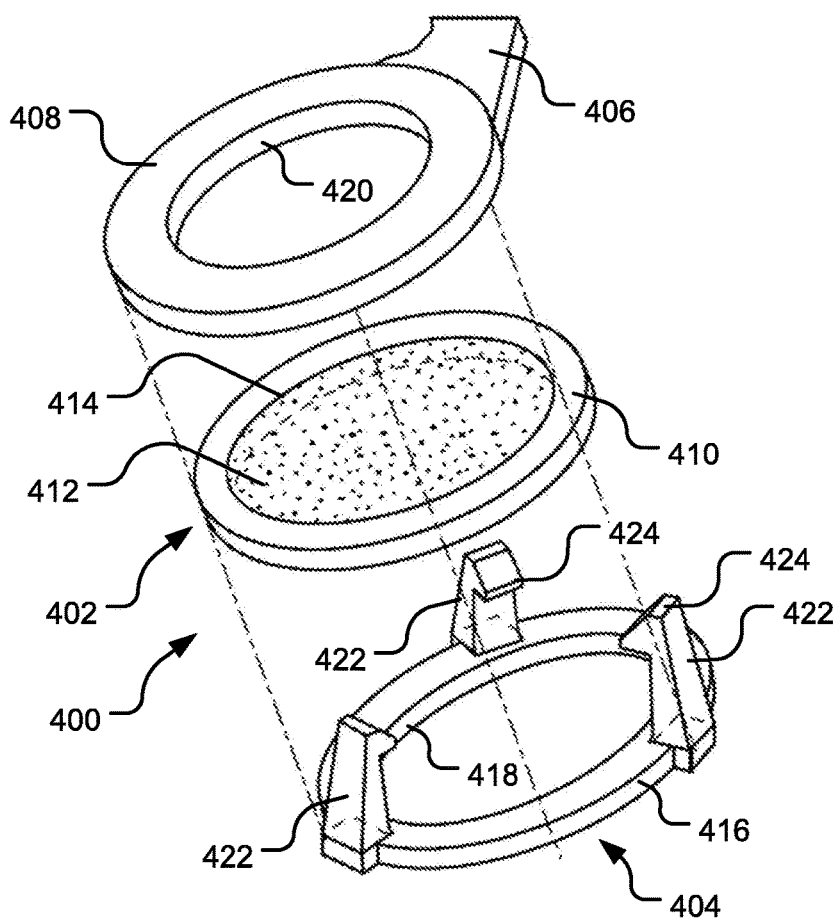
FIG. 5 illustrates an exploded isometric view of an active constraint device for a laparoscopic instrument according to one or more aspects of the present disclosure.
Figure 6A:
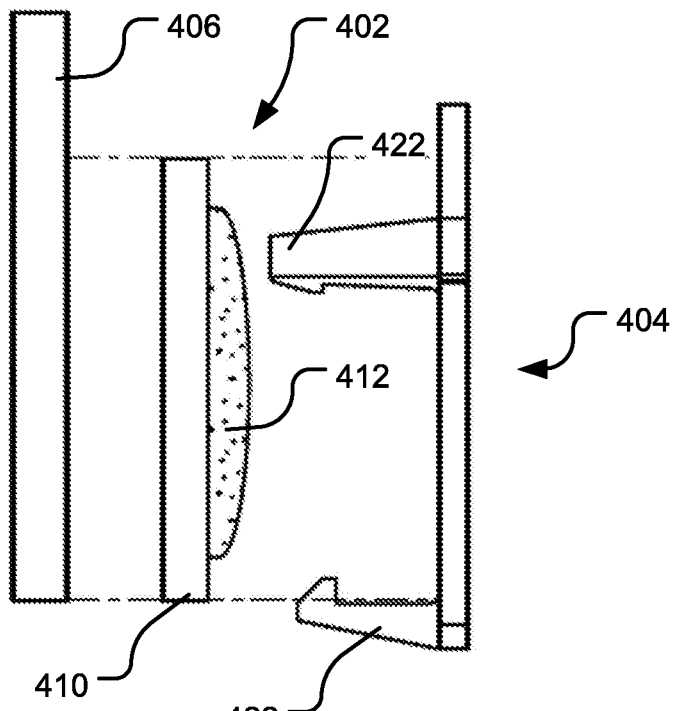
FIG. 6A illustrates an exploded side view of an active constraint device for a laparoscopic instrument according to one or more aspects of the present disclosure.
Figure 6B:
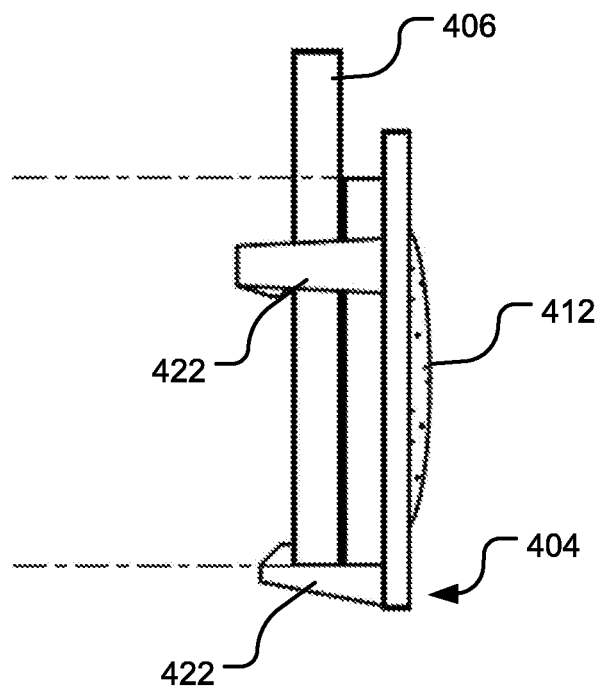
FIG. 6B illustrates an assembled side view of an active constraint device for a laparoscopic instrument according to one or more aspects of the present disclosure.
Figure 7:
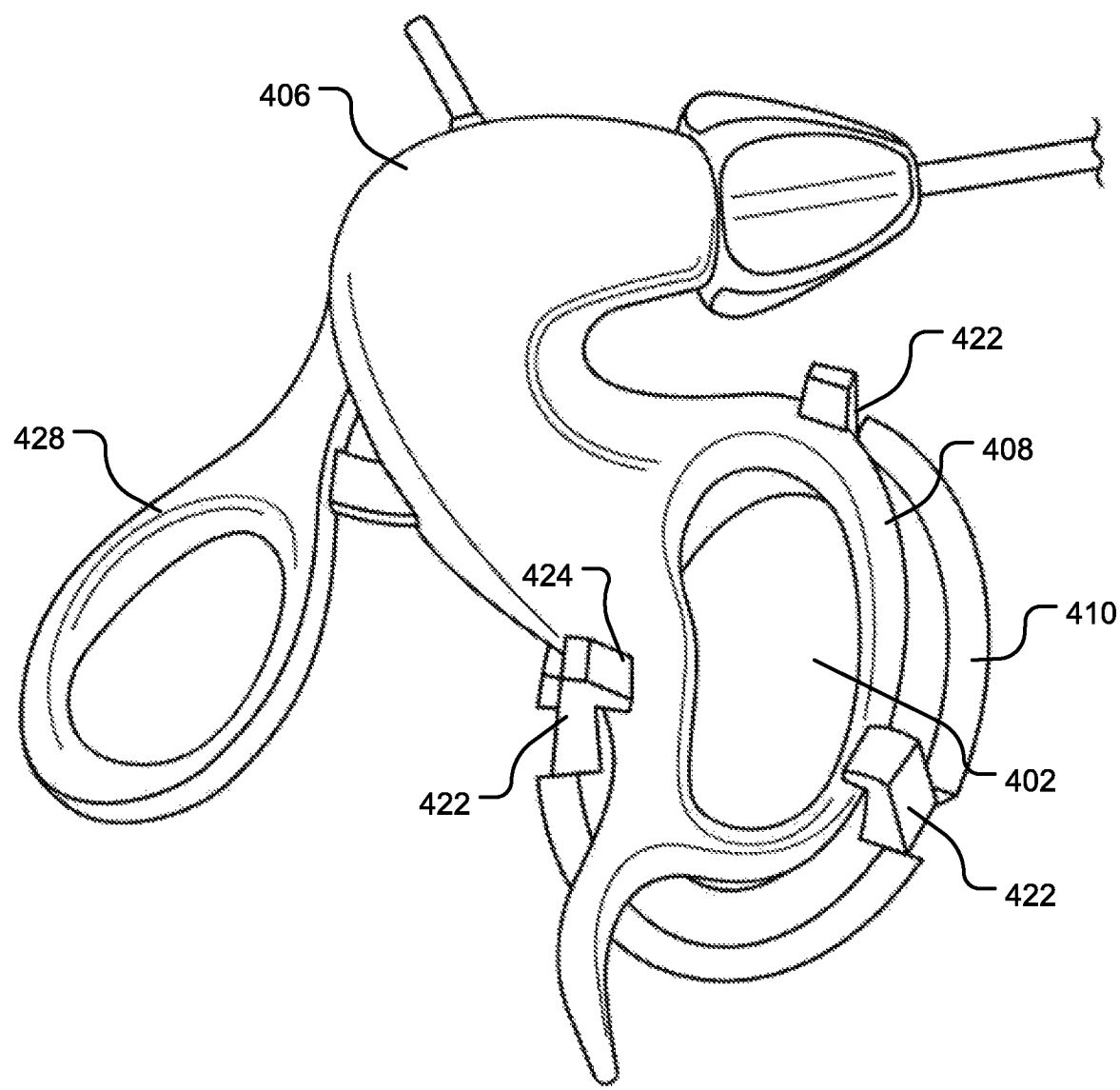
FIG. 7 illustrates an active constraint device attached to a laparoscopic instrument in accordance with an embodiment of the present disclosure.
Figure 8:
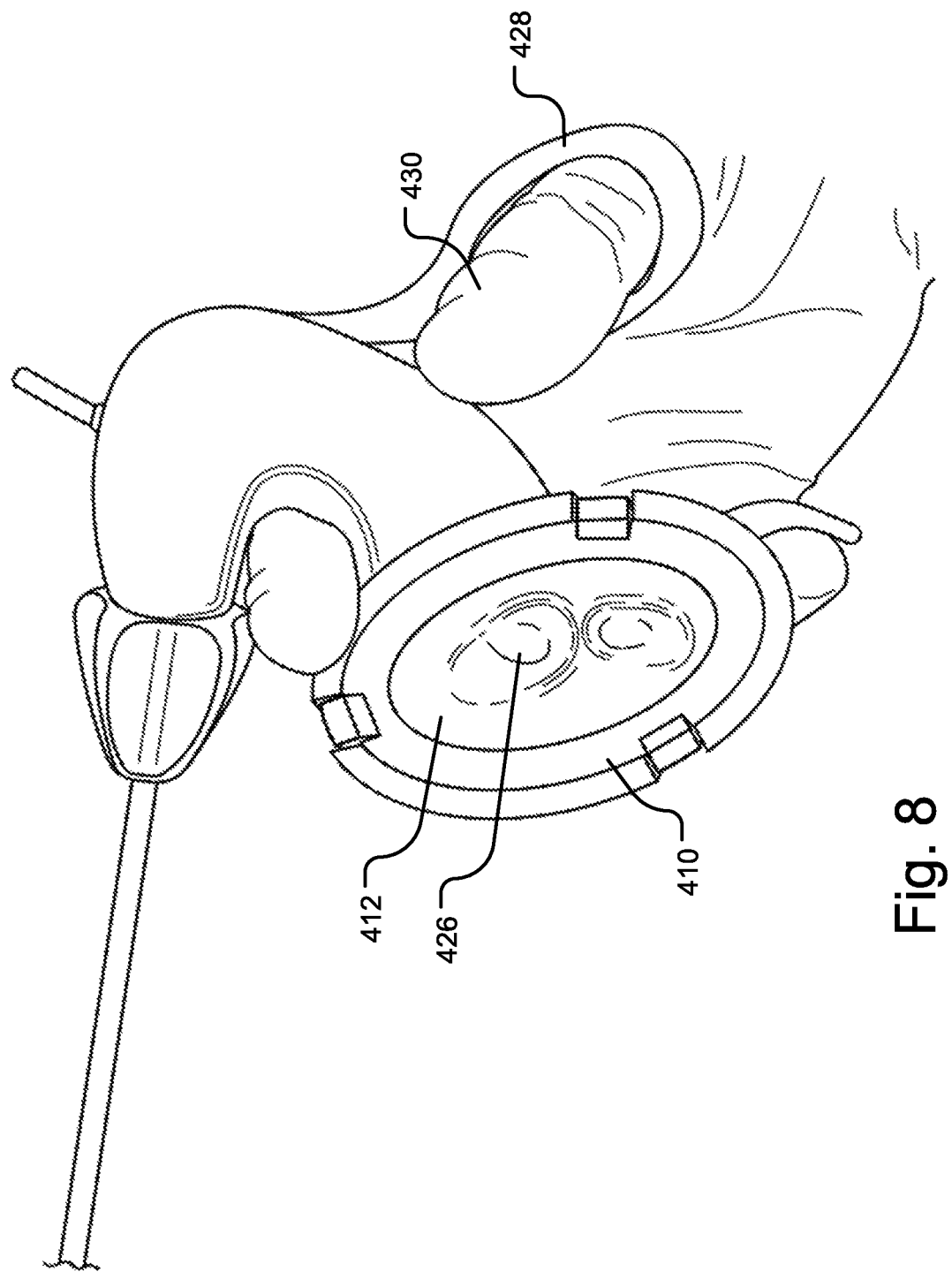
FIG. 8 illustrates an active constraint device attached to a laparoscopic instrument and in use in accordance with an embodiment of the present disclosure.

The disclosure now turns to FIGS. 4-8 to illustrate one embodiment of an active constraint device 400 for a laparoscopic instrument 406, or a constraint that exhibits or provides dynamic force feedback to the user of the laparoscopic instrument 406, in accordance with aspects of the present disclosure. In particular, FIG. 4 illustrates a front view of an active constraint device 400, FIG. 5 illustrates an exploded isometric view of the active constraint device 400, FIG. 6A illustrates an exploded side view of the active constraint device 400, FIG. 6B illustrates an assembled side view of the active constraint device 400, and FIG. 7 illustrates the active constraint device 400 attached to a laparoscopic instrument 406, and FIG. 8 illustrates the active constraint device 400 attached to the laparoscopic instrument 406 and in use. Similar to the passive constraint device 100 discussed above, the active constraint device 400 may attach to a laparoscopic instrument 406 and kinematically prevent the user of the laparoscopic tool from over-gripping the tool when being held. More particularly, the active constraint device 400 may attach to one or more finger loops of a laparoscopic instrument 406 to prevent a user's fingers from extending fully through the finger loops. Rather, the active constraint device 400 provide a resistive force against the user's fingers when placed through the finger loops of the tool 406, directing the user to grip the tool 406 properly for efficient and effective use during a surgical procedure.

In general and as illustrated best in FIGS. 4-6B, the active constraint device 400 may include an elastic finger guard 402 and a fastening clip 404. The fastening clip 404 may attach the finger guard 402 onto the laparoscopic instrument 406, and more particularly may attach the finger guard 402 to the laparoscopic instrument 406 to cover a finger hole or finger loop 408 of the tool and restrict insertion of a user's finger through the finger hole 408 of the tool 406. As shown in the implementation of FIG. 5, the finger guard 402 of the active constraint device 400 may include a support frame 410 attached to an elastic or other flexible membrane 412 disposed within the support frame 410, the membrane 412 connected to the support frame 410 at interface 414. The fastening clip 404 may include an oval ring 416 with an inner opening 418 to approximately match an inner circumference 420 of an oval finger hole or finger loop 408 of the laparoscopic instrument 406 when assembled. Interface 414 similarly approximately matches the inner opening 418 of the fastening clip 404 and the inner circumference 420 of the finger loop 408 when assembled. A set of snap-on prongs 422 are attached to the fastening clip 404 and may include one, two, three, or more prongs. Each of the snap-on prongs 422 may include a triangular, flared end 424 away from the fastening clip 404 and may be constructed of a flexible material that enables to the snap-on prongs 422 to be urged outward during mounting on the laparoscopic instrument 406. FIGS. 6A and 6B illustrate the attachment of the active constraint device 400 to the finger loop 408 of the laparoscopic instrument 406. Once the fastening clip 404 is attached to the laparoscopic instrument 406, the snap-on prongs 422 may spring back to a resting position in which the triangular, flared ends 424 attaches the active constraint device 400 onto the laparoscopic instrument 406. A similar force applied to the snap-on prongs 422 may cause release of the active constraint device 400 from the laparoscopic instrument 406. When mounted, the snap-on prongs 422 hold the active constraint device 400 firmly against the finger loop 408 and securely hold finger guard 402 in place between the fastening clip 404 and finger loop 408.

FIGS. 7 and 8 show an active constraint device 400 attached to laparoscopic instrument 406 at the finger loop 408 wherein snap-on prongs 422 are snapped to finger loop 408. As shown, the snap-on prongs 422 hold the active constraint device 400 firmly against the finger loop 408 and securely hold the finger guard 402 in place between the fastening clip 404 and finger loop 408 and over the inner circumference 420 of the finger loop. As shown in FIG. 8, the active constraint device 400 may resist extension of a user's fingers 426 entirely through the finger loop 408. More particularly, the fingers 426 of the user contact the finger guard 402 of the active constraint device 400 and are prevented from extending through the elastic guard. In an alternate use, the active constraint device 400 may be fit to a thumb loop 428 of the laparoscopic instrument 406 to constrain thumb 430 position while in use. In yet another use, two active constraint devices 400 may be used, one attached to the finger loop 408 and another attached to the thumb loop 428 of the laparoscopic instrument 406. In other embodiments, the positions of the snap-on prongs 422 may be configured so that active constraint device 400 may be used on the left side or the right side of finger loop 408 and/or the thumb loop 428 to accommodate right-handed users or left handed users, respectively.

In one particular implementation, the finger guard 402 may be constructed of cured, pourable silicone in a custom three-dimensional printed mold. The silicone elastic finger guard 402 may be oval in shape and have a minor diameter of 1.875 inches and a major diameter of 2.7 inches, with dimensions driven by the shape of a common laparoscopic instrument. The thickness of the finger guard 402 may be thinnest in the middle and thicker towards the outer edges to maximize both the stretch of the active constraint device 400, as well as durability. The thickness of the finger guard 402 may range from approximately 0.0285 to 0.189 inches. The fastening clip 404 may be three-dimensional printed to securely attach the silicon elastic finger guard 402 to the laparoscopic instrument 406. In one instance, the fastening clip 404 may include three snap-on prongs 422 with two in line with each other and one centered between the inline prongs. The fastening clip 404 may also be oval in shape, with a minor diameter of 1.6 inches and a major diameter of 2.6 inches. The two inline prongs may be separated by 1.7 inches and the third prong may be separated from the two inline prongs by 2 inches. While an embodiment of the active constraint device 400 has been constructed with the particular dimensions and shapes as noted, the active constraint device 400 should not be limited to such sizes, or even scaled in a precise manner. In the spirit of the present disclosure, there are many different types of laparoscopic instruments for which the shape of the finger guard 402, fastening clip 404, and/or the snap-on prongs 422 of the active constraint device 400 may vary from the shape described and indicated in FIGS. 4-6B. Furthermore, the opening size of the finger guard 402 and/or fastening clip 404, for example, may vary in relation to the opening size of the finger loop 408 (or thumb loop 428). The number of snap-on prongs 422 of the fastening clip 404 may also vary in other embodiments.

In another embodiment illustrated in FIGS. 9A-9C, an active constraint device 900 may include a solid, a non-elastic finger guard 902, a fastening clip 904, and a set of elastic bands or elastic connectors 924 that attach the active constraint device 900 onto a laparoscopic instrument 906. As shown in FIGS. 9A-9C and similar to the active constraint device 600 discussed above, the active constraint device 900 of FIGS. 9A-9C may comprise the finger guard 902 and a fastening clip 904. However, in this embodiment, the finger guard 902 may include a frame 910 attached to an inelastic membrane 912, the frame 910 connected to the inelastic membrane at interface 914. In one embodiment, the membrane 412 includes a curved surface 926 extending away from the finger loop 908 of the laparoscopic instrument 906 to which the finger guard 902 may be attached. The depth of the curved surface 926 may vary in different embodiments of the active constraint device 900 to provide for more or less extension of a user's fingers through the corresponding finger loop 908. Fastening clip 904 may include an oval ring with an inner opening 918 to approximately match an oval finger hole or finger loop 920 of the finger loop 908 of the laparoscopic instrument 906. The interface 914 of the finger guard 902 approximately matches the inner opening 918 of the fastening clip 904 and the finger loop 920 when assembled. A set of protrusions 922 may extend from a lower surface of the fastening clip 904 and, when the active constraint 900 is mounted to the laparoscopic instrument 906, the elastic connectors 924 may twist around finger loop 908 and fasten to the set of protrusions 922 to securely hold the finger guard 902 in place between fastening clip 904 and finger loop 908 during use.

While embodiments of the active constraint device 400, 900 may be constructed with particular dimensions and shapes, the constraint should not be limited to sizes shown, or even scaled in a precise manner. In the spirit of the present disclosure, there are many different types of laparoscopic instruments for which the shape of the finger guard 402, 902, prongs 422 or protrusions 922, and/or the elastic connectors 924 of the active constraint device may vary from the shape described and indicated. Furthermore, the opening size of the finger guard 402, 902 and/or fastening clip 404, 904, for example, may vary in relation to the opening size of the finger loop 408, 908 (or thumb loop). The number of the elastic connectors 924 may also vary in other embodiments. In some embodiments the finger guard 402, 902, fastening clip 404, 904, and/or prongs 422 or protrusions 922 may be a single molded part.

Figure 10:
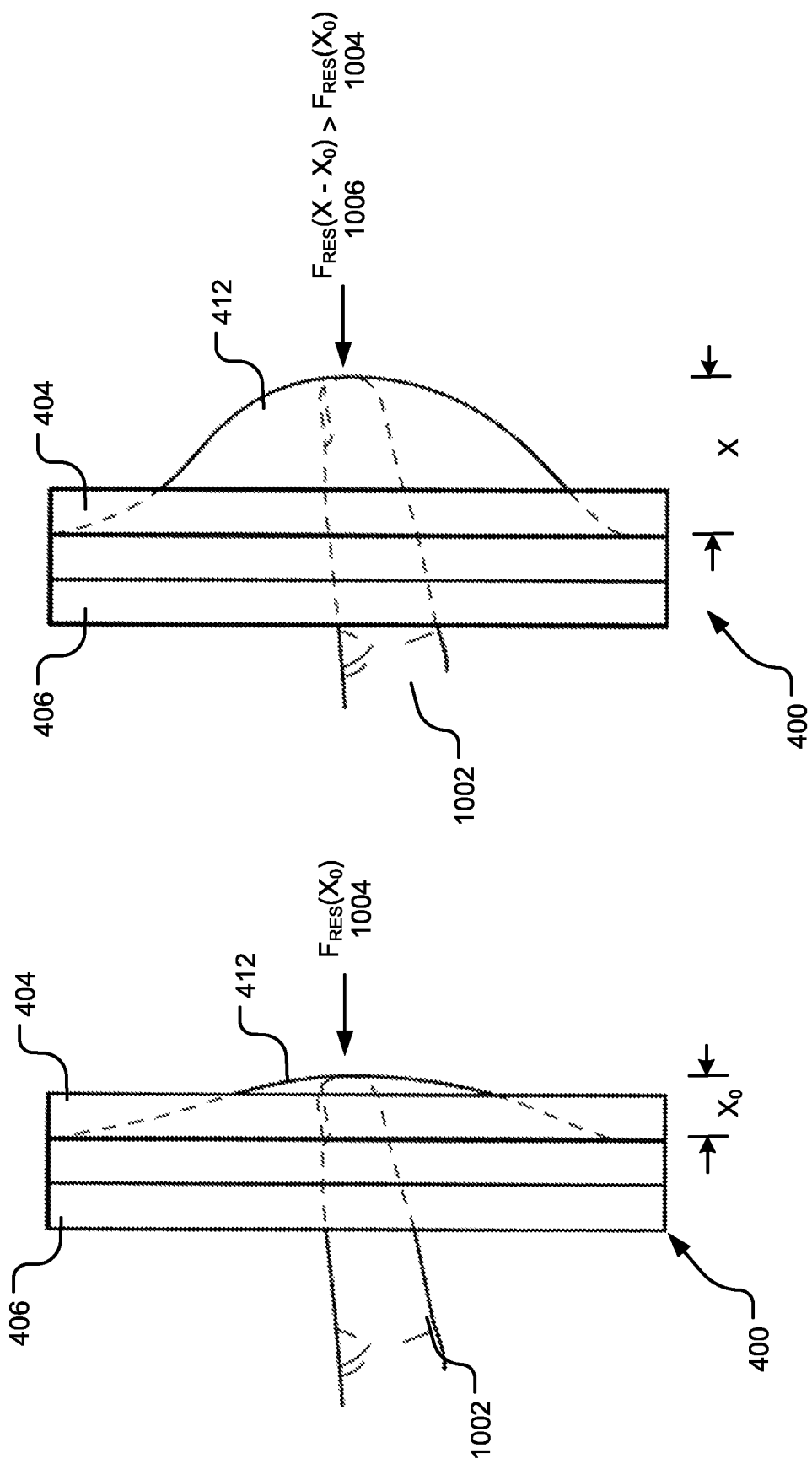
FIG. 10 illustrates a resistive force for dynamic feedback for an active constraint device with an elastic finger tray in accordance with the present disclosure.

As described above, the active constraint device 400, 900 may provide a resistive force against a user's fingers when attached to the laparoscopic instrument 406, 906 and prevent insertion of the fingers fully through the finger loop 408, 908. For example, FIG. 10 illustrates a resistive force for dynamic feedback for a first active constraint device 400 with an elastic finger guard 402 such as that described above in relation to FIGS. 4-8. Similar to above, the active constraint device 400 may include an elastic guard including a support frame 410 attached to an elastic or other flexible membrane 412 disposed within the support frame 410. The elastic guard may be attached to a finger loop of the laparoscopic instrument 406 by a fastening clip 404. When the tool is in use, a user's finger 1002 may be pressed against the membrane 412 of the elastic guard. When the user's finger 1002 is at position $x_0$, the user may experience a minimal resistive force $F_{RES}(x_0)$ 1004. However, as the user applies a larger force against the membrane 412, the user may experience a larger resistive force. In particular, when the user's finger 1002 is at position x, the membrane 412 of the finger guard stretches so that user experiences a resistive force proportional to over-gripping $F_{RES}(x-x_0)$ 1006, which is greater than the resistive force $F_{RES}(x_0)$ 1004 at position $x_0$. This additional resistive force $F_{RES}(x-x_0)$ 1006 provides a resistive feedback to the user to direct the user to a proper grip of the laparoscopic instrument to which the active constraint device 400 is attached.

Figure 11:
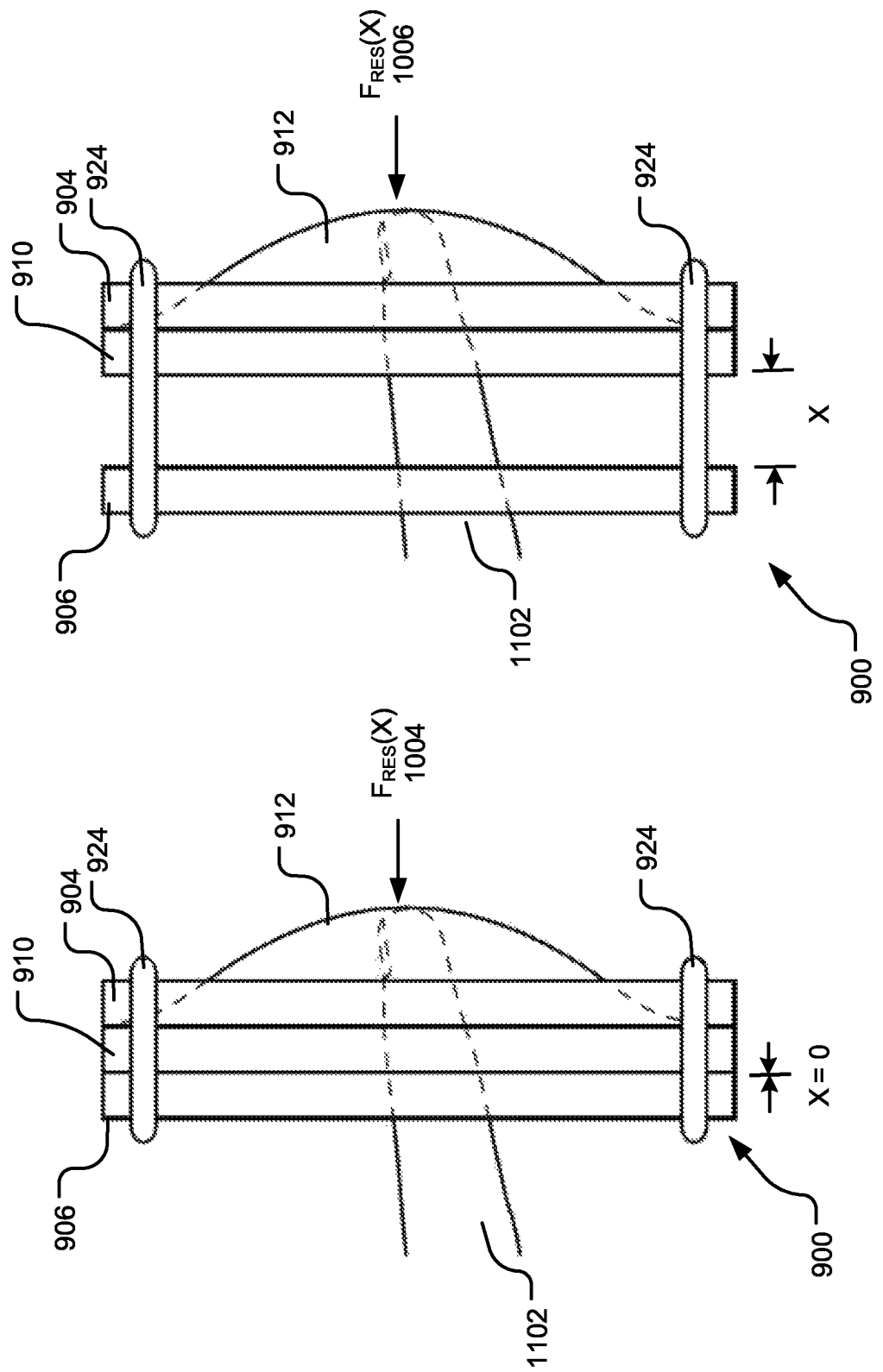
FIG. 11 illustrates a resistive force for dynamic feedback for an active constraint device with a solid finger tray connected to finger loops via elastic connectors in accordance with the present disclosure.

Similarly, FIG. 11 illustrates a resistive force for dynamic feedback for a second active constraint device 900 with the finger guard 902 such as that described above in relation to FIG. 9. As shown, the active constraint device 900 may include the finger guard 902 attached to a finger loop of the laparoscopic instrument 906 by a fastening clip 904. When the tool is in use, a user's finger 1102 may be pressed against the inflexible membrane 912 of the elastic guard. When the user's finger 1002 is at position $x_0$, the user may not experience a resistive force such that $F_{RES}(x_0)=0$ 1004. As the user applies a larger force against the inflexible membrane 912, the elastic connectors 924 attaching the fastening clip 904 to the laparoscopic instrument 906 may stretch to allow horizontal movement of the finger guard 902 and the fastening clip 904. The stretching of the elastic connectors 924 may generate an opposing force against the user's finger 1102 to resist the finger's movement. In particular, when the elastic connectors 924 are stretched to width x, the user experiences the resistive force $F_{RES}(x)$ 1006 proportional to over-gripping, which is greater than the resistive force $F_{RES}(x_0)$ 1004 at position x. The resistive force $F_{RES}$ 1006 provides a resistive feedback to the user to direct the user to a proper grip of the laparoscopic instrument to which the active constraint device 900 is attached.

Figure 12:
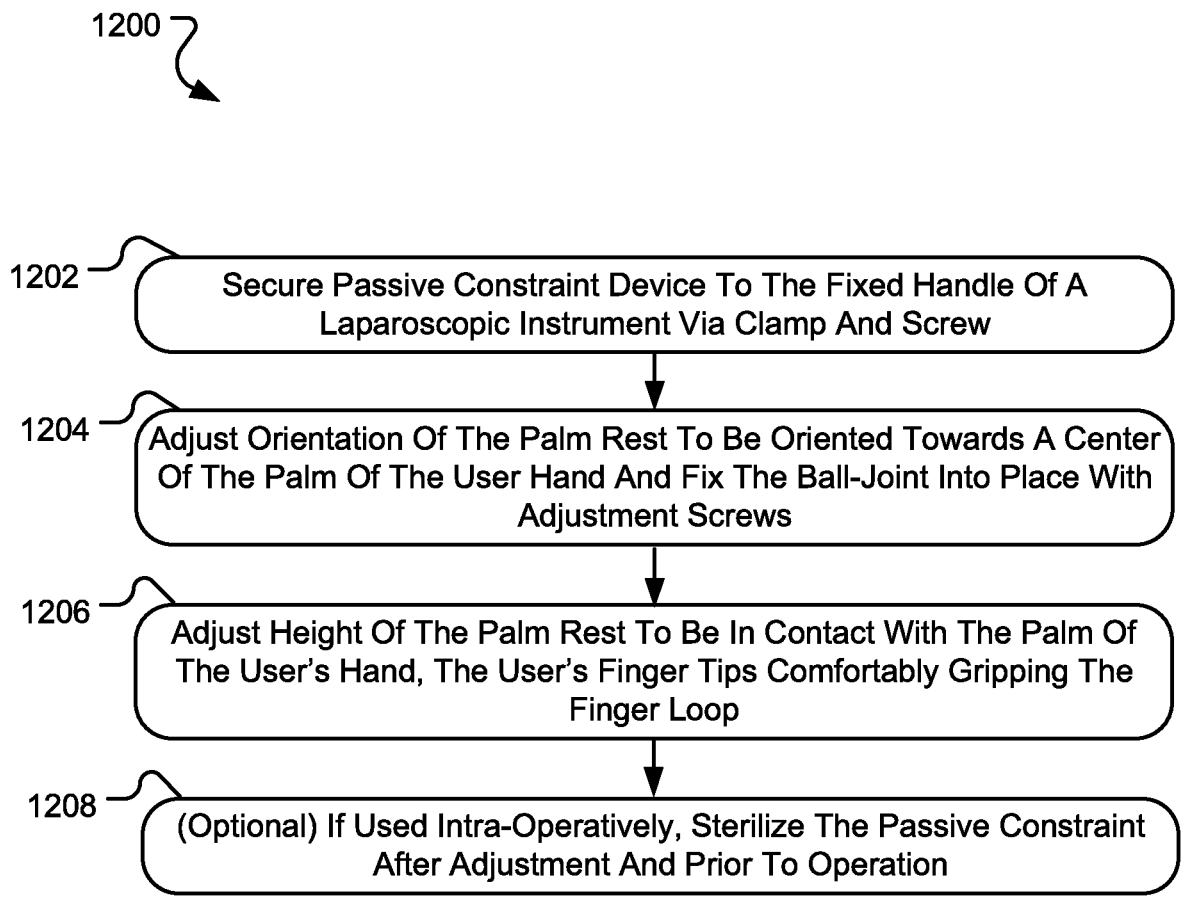
FIG. 12 is a flowchart illustrating a method for use of a passive constraint device in accordance with the present disclosure.

FIG. 12 is a flowchart illustrating a method 1200 for use of a passive constraint device 100 in accordance with the present disclosure, the method being appropriate for a passive constraint device such as passive constraint device 100 of FIGS. 1-3B. The method 1200 begins at step 1202 wherein the passive constraint device 100 is secured to the fixed handle of laparoscopic instrument 102 by attaching the clamp portion 104 of the constraint device 100 to the main body of the laparoscopic instrument and adjusting the clamp screw 118 to tighten the screw against the main body of the laparoscopic instrument. At step 1204, the position of the palm rest 122 may be adjusted via the joint portion 106 to be oriented towards the center of the palm 308 of the user's hand 310. Then the joint portion 106 is fixed in place with the adjustment screws 112, 120. At step 806, the height of the palm rest 122 is adjusted via the locking nut 114 so that the palm rest 122 is in contact with the palm 308 of the user's hand 310, wherein the user's finger tips comfortably grip the finger loop 306 of the laparoscopic instrument 102 without over-gripping. Optionally, at step 808, the passive constraint device 100 is used intra-operatively by first sterilizing the passive constraint device after the above steps, but prior to start of the operational procedure.

Figure 13:
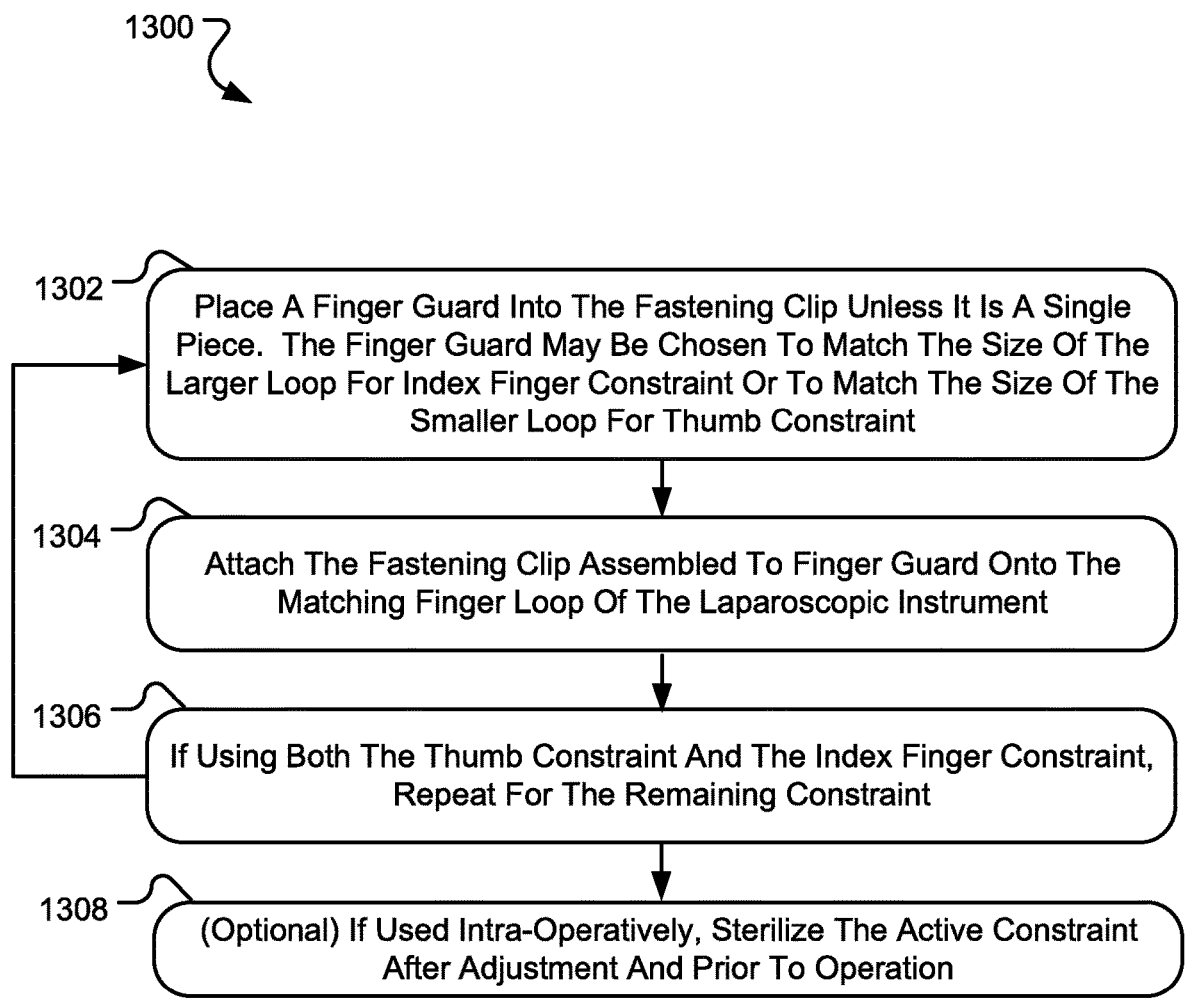
FIG. 13 is a flowchart illustrating a method for use of an active constraint device in accordance with the present disclosure.

FIG. 13 is a flowchart illustrating a method 1300 for use of an active constraint device 400 in accordance with the present disclosure, the method being appropriate for an active constraint device such as the constraint device 400 of FIGS. 4-8 or active constraint device 900 of FIGS. 9A-9C. The method begins at step 1302 wherein an appropriate finger guard 402 is chosen to match the size of the finger loop for index finger constraint or to match the size of the thumb loop for a thumb constraint. If the finger guard 402 and fastening clip 404 is made as a single piece, then remaining steps are completed, otherwise the finger guard 402 is assembled together with a fastening clip 404. At step 1304, the finger guard and fastening clip assembly is attached onto the matching finger loop 408 of the laparoscopic instrument 406. For a constraint device 400 with a snap-on prong 422, then the constraint device 400 is clipped on the matching finger loop 408. For an active constraint device 900 with elastic connectors 924, the constraint device 900 is attached to the matching finger loop 908 via the elastic connectors 924 and protrusions 922. At step 1306, if two constraints are being used, repeat steps 1302 and 1304 for the remaining constraint. Optionally, at step 1308, when the active constraint device 400, 900 is used intra-operatively, sterilize the passive constraint device after assembly is complete including steps 1302, 1304 and 1306 and any repetition for multiple loops, but prior to start of the operational procedure.

III. Experimental Methods

Figure 14:
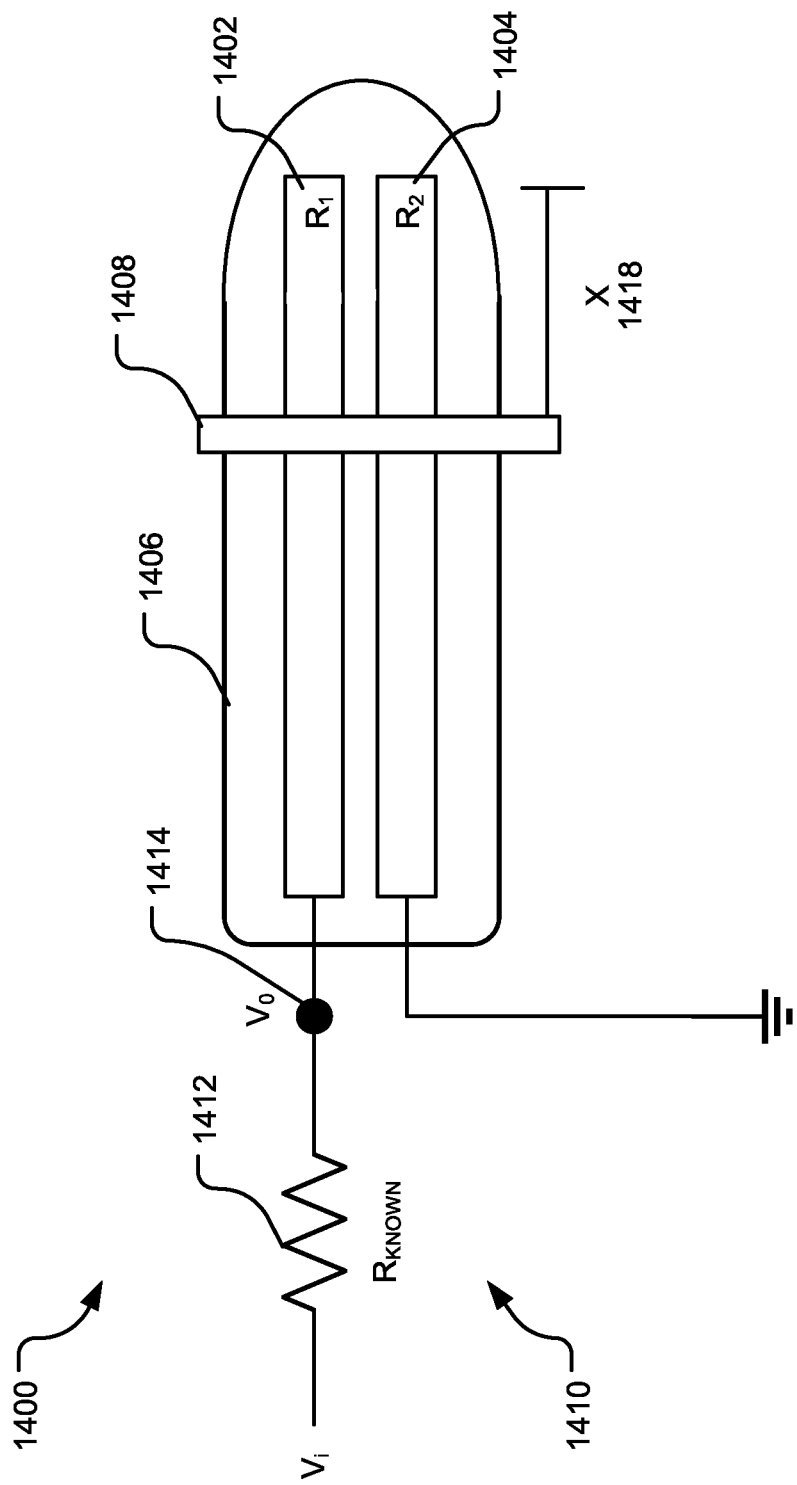
FIG. 14 shows an embodiment of sensor circuitry for tracking the location of the laparoscopic instrument in relation to a user's finger while wearing the sensorized gloves in accordance with the present disclosure.

The disclosure now turns to methods and devices for testing the effectiveness of the above disclosed constraint devices. In one method, a custom sensorized glove may be utilized to measure the position of the tool along each finger. For example, FIG. 14 shows an embodiment of sensor circuitry 1400 for tracking the location of the laparoscopic instrument in relation to a user's finger while wearing a sensorized glove in accordance with the present disclosure. In particular, each finger of the sensorized glove may include two or more conductive fabric traces 1402, 1404 sewn onto a fabric finger pad 1406. The finger pad 1406 may be adhered to a standard medical glove or any other glove on the subjects hand with a double sided adhesive or other attachment device. A metallic tool 1408 (or plastic tool covered with adhesive metal foil), may slide along the finger pad 1406 during use of the tool and may behave like a potentiometer. A voltage divider circuit 1410 may convert measured voltages to the tool 1408 position and may be normalized for each finger. The circuit 1410 may include a positive volt reference signal ($V_i$), a known resistor 1412 and an analog input to the digital-to-analog converter ($V_o$) 1414. The position of the tool 1408 along the finger, x 1418, is a function of the two conductive traces ($R_1$ 1402 and $R_2$ 1404), a resistivity of the fabric (r), and a cross-sectional area of a trace (A). Using standard equations for a voltage divider and the resistance of a wire, it can be shown that the position of the instrument along the finger, x 1418, can be obtained from:

$$x = \frac{Vo * Rknown}{Vi} * \frac{A}{\rho}$$

Using the sensorized glove, training trials were performed of various tasks, including a peg transfer task to move six rubber blocks from one side of the board to the other, and back, without drops and a circle cutting task to cut out a circle shape which is printed on a two-ply piece of medical gauze using one grasper and one cutter. Errors are assigned if the cut is more than 2 mm off the circle boarder. The tasks were performed while using one of the passive or active constraints or no constraint. The effects of constraint type, task type, and finger were evaluated for each of an overall length of the trial, an average tool position ratio (1.0 corresponds to tool at fingertip, 0.0 corresponds to tool at finger base), an average drop time (i.e., time of finger not in contact with tool), and variabilities of tool position. During a drop, because the finger is not in contact with the tool at all, the resistance of the sensor is infinite, the voltage recorded is then pulled up to the supply voltage (Vi). As expected, the passive constraint device shows significantly farther tool positions (i.e., less over-grip) than the active and no constraint conditions. The no constraint condition had significantly lower non-contact times than the other conditions (i.e., less finger drops), likely due to over-gripping the tool. The passive constraint also showed significantly shorter overall task times.

The fingers which exhibited significantly less over-grip than the others were the left (non-dominant) index finger, and right (dominant) middle and ring fingers. These same fingers, along with the left pinky also showed the lowest amounts of non-contact or drop time, indicating the role of these fingers in manipulating the tool. The left thumb, right index, and right pinky fingers showed significantly less variability in tool position than the other fingers, indicating the role of these fingers in stabilizing the grip.

Referring now to FIG. 15, a general method 1500 for training surgical residents in the proper handling of laparoscopic instruments is provided. The method 1500 utilizes passive and active constraints of the present disclosure in a surgical residency training program. A typical surgical residency program is for four years following graduation. Thus, at step 1502, a set of incoming surgical residents are provided at least one constraint device (active or passive) which is used without removal during the first year of the training program. During the second year (Post-Grad Year 1), for example, at step 1504, constraint devices are allowed to be removed. This would occur upon successful completion of the training program, determined by examination and observation of laparoscopic operational procedures. Based on further observation, during years Post-Grad Year 3 and Post-Grad Year 4, any given surgical resident that requires some level of remediation is required to utilize a constraint device to correct a particular problem in gripping and handling the set of laparoscopic instruments (step 1506). Some delicate procedures, for example, certain pediatric surgeries, benefit from the use of laparoscopic constraints as taught herein. Thus the practicing surgeon, at step 1508, may choose to use a passive or an active constraint during surgery to improve outcomes. In the spirit of the present disclosure, the method 1500 should not be limited to the exact years shown for a surgical residency program, but may vary according to practices adopted by a particular residency program.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. A method for training for use of a laparoscopic instrument in a surgical procedure, the method comprising:
   securing a constraint device too laparoscopic instrument to enable controlling of the laparoscopic instrument during a procedure with the constraint device attached to the laparoscopic instrument, and
   adjusting the constraint device to restrict extension of an instrument operator's fingers through a finger hole of the laparoscopic instrument for proper grip of the laparoscopic instrument during the procedure,
   wherein,
      the constraint device includes (i) a connector operable to secure the constraint device to the laparoscopic instrument, and (ii) an adjustable palm contact portion operable to orient the instrument operator's fingers during the procedure.

2. The method of claim 1, wherein the constraint device includes a finger guard and an attachment clip operable to orient the finger guard over the finger hole when attached to the laparoscopic instrument.

3. The method of claim 2,
   wherein,
      the finger guard is composed of a flexible material, and
      the finger guard is operable to provide a resistive force against the instrument operator's fingers during control of the laparoscopic instrument.

4. The method of claim 3,
   wherein,
      the attachment clip includes a circular frame and an attachment prong extending from the circular frame, and
      the attachment prong includes a flared end opposite the circular frame to hold the attachment clip and the finger guard to the finger hole of the laparoscopic instrument.

5. The method of claim 2,
wherein,
the finger guard is composed of an inflexible material, and
the attachment clip includes a circular frame and a plurality of attachment protrusions extending from the circular frame.

6. The method of claim 5, wherein the constraint device includes an elastic connection band extending between the plurality of attachment protrusions and over the finger hole to hold the attachment clip and the finger guard to the finger hole of the laparoscopic instrument.

7. The method of claim 1, wherein the connector is a clamp.

8. The method of claim 7,
wherein,
the constraint device includes a ball and socket joint secured to the clamp and the adjustable palm contact portion, and
the ball and socket joint includes at least one locking mechanism operable to maintain the ball and socket joint in a fixed position relative to the laparoscopic instrument during the procedure.

9. The method of claim 8,
wherein,
the adjustable palm contact portion includes a palm rest and a palm rest stem extending from the palm rest, and
the palm rest stem is adjustably secured to the ball and socket joint via the palm rest stem.

10. The method of claim 9,
wherein the adjusting of the constraint device includes:
orienting the ball and socket joint to locate the palm rest in an orientation relative to a center of an operator's palm; and
locking the ball and socket joint in the orientation via the at least one locking mechanism.

11. The method of claim 10,
wherein,
the at least one locking mechanism includes a plurality of locking mechanisms, and
the locking of the ball and socket joint in the orientation includes rotating at least one of the plurality of locking mechanisms.

12. The method of claim 9,
wherein the adjusting of the constraint, device includes:
adjusting an insertion depth of the palm rest stem within the ball and socket joint; and
setting, via a locking nut disposed on the palm rest stem, the insertion death the palm rest stem within the ball end socket joint.

13. The method of claim 1, wherein the constraint device includes a receiver operable to receive a portion of the laparoscopic instrument within the constraint device.

14. A device for training an operator to use a laparoscopic instrument in a surgical procedure, the device comprising:
a finger guard including a circular support frame and a membrane spanning an inner portion of the circular support frame; and
an attachment clip including an outer ring and a plurality of attachment prongs extending from the outer ring, the attachment clip attached to an outer surface of a finger hole of a laparoscopic instrument to orient the finger guard against an opening of the finger hole, the membrane of the finger guard covering the opening of the finger hole.

15. The device of claim 14, wherein the finger guard is composed of a flexible material to restrict extension of an instrument operator's fingers through the finger hole of the laparoscopic instrument.

16. The device of claim 14, wherein each of the plurality of attachment prongs includes a flared end opposite the circular support frame to hold the attachment clip and the finger guard to the outer surface of the finger hole of the laparoscopic instrument.

17. The device of claim 14, further comprising:
an elastic connection band extending between the plurality of attachment prongs and over the outer surface of the finger hole to orient the finger guard against the opening of the finger hole.

18. The device of claim 14, wherein a first inner circumference of the outer ring and a second inner circumference of the circular support frame are substantially similar to a third inner circumference of the finger hole of the laparoscopic instrument.

19. A constraint device for training a medical professional to use a laparoscopic instrument in a surgical procedure, the device comprising:
a clamp portion including a clamping mechanism to attach the constraint device to the laparoscopic instrument;
an adjustable joint attached to the clamp portion;
a palm rest stem extending from the adjustable joint; and
a palm contact attached to an end of the palm rest stem opposite of the adjustable joint, the palm contact adjustable to contact a palm of a hand of an operator of the laparoscopic instrument during use of the laparoscopic instrument.

20. The constraint device of claim 19, wherein the adjustable joint includes a ball and a socket joint with three degrees of freedom of movement.

* * * * *